United States Patent [19]

Volynsky et al.

[11] 3,973,004

[45] Aug. 3, 1976

[54] METHOD OF PRODUCING FOLLICLE-STIMULATING HORMONE

[76] Inventors: Alexandr Semenovich Volynsky, ulitsa Gogolya, 75; Mikhail Ivanovich Prokofiev, ulitsa Khodzhaeva, 2; Aida Pavlovna Kryachkova, ulitsa Ustobaeva, 43, all of Tashkent, U.S.S.R.

[22] Filed: Dec. 7, 1972

[21] Appl. No.: 312,866

[30] Foreign Application Priority Data

Dec. 7, 1971   U.S.S.R............................ 1721918

[52] U.S. Cl................................. 424/108; 424/109
[51] Int. Cl.².......................................... A61K 35/46
[58] Field of Search........................... 424/108, 109

[56] References Cited
UNITED STATES PATENTS

| | | | |
|---|---|---|---|
| 2,256,920 | 9/1941 | Allers et al. | 424/108 |
| 2,312,901 | 8/1943 | Riehen et al. | 424/108 |
| 2,356,803 | 8/1944 | Van Dyke et al. | 424/108 |

FOREIGN PATENTS OR APPLICATIONS

| | | | |
|---|---|---|---|
| 1,199,924 | 1965 | Germany | 424/108 |

OTHER PUBLICATIONS

Weisenberg et al., Biochemistry vol. 7, No. 12, pp. 4466–4479 Dec., 1968.

*Primary Examiner*—Stanley J. Friedman
*Attorney, Agent, or Firm*—Holman & Stern

[57] ABSTRACT

A method of producing follicle-stimulating hormone (FHS) from sheep pituitary glands by disintegrating the pituitaries, extracting the latter with an approximately 0.2 molar solution of ammonium sulphate followed by bringing the pH of the solution to 5.5, separating the thusobtained extract into a supernatant and liquid and precipitate. Purification of FSH contained in the supernatant liquid is carried out by saturating the liquid with dry ammonium sulphate until a concentration of ammonium sulfate in the obtained solution of 40–50 percent of saturation is obtained the pH of the solution is adjusted to 7.4–7.5 and the resultant precipitate is separated from the supernatant liquid which is saturated with dry ammonium sulphate to a concentration in the obtained solution of 70–80 percent of saturation to obtain a precipitate which is treated with the ammonium sulphate solutions whose concentration is selected from the range of 56–58 percent of saturation, to form filtrates and subsequently precipitate FSH from the filtrates by saturating these with dry ammonium sulphate to a concentration thereof equal to 70–80 percent in the solutions obtained (of concentrated one), with subsequent bringing the pH of the solutions to 4.5 and isolation of the purified hormone from the supernatant liquid.

8 Claims, No Drawings

METHOD OF PRODUCING FOLLICLE-STIMULATING HORMONE

The present invention relates to a method of producing follicle-stimulating hormone (FSH). The harmone can be used in the manufacture of endocrinous preparations.

A method of producing FSH which makes use of a multistaged technique for purification of FSH on cellulose and sephadexes is known in the art. Purification by said method is accompanied by heavy losses of the hormone exceeding 90 percent of the initial amount so that the yield of the final product is too low being as little as 7.6 percent. The process takes much time and labour and involves the use of highly valuable reagents.

Another method of producing FSH is known in the art, by which the hormone is obtained from sheep pituitary glands by homogenization of the latter and extraction with a solution of $Ca(OH)_2$ followed by separation of the resultant extract into a supernatant liquid and precipitate. According to said method purification of FSH from the supernatant liquid is carried out by way of successive precipitation and reprecipitation of FSH from the pituitaries with ammonium sulphate solutions of rising concentrations. The yield of FSH resulting from such a purification is rather low, viz., 0.5 unit in equivalents as per standard NiH—FSH—Si of the National Institute of Health (USA).

It is an object of the present invention to provide a method of producing follicle-stimulating hormone from sheep pituitary, that enables a higher yield of the final product and simpler process technology involving the use of inexpensive reagents.

According to said and other objects the invention, pituitaries are disintegrated and extracted, the resultant extract is separated into a supernatant liquid and a precipitate, whereupon FSH contained in the supernatant liquid, is purified.

According to the invention, extraction of pituitaries is carried out with an approximately 0.2-molar ammonium sulphate solution, followed by bringing the pH value to 5.5, whereas purification of FSH is performed by saturating supernatant liquid with dry ammonium sulphate to a concentration of 40–50 percent of saturation in the solution obtained, with subsequent adjustment of pH value to 7.4–7.5 and separating the resultant precipitate from the supernatant liquid which is then saturated with dry ammonium sulphate to a concentration of 70–80 percent of saturation in the thus-obtained solution, followed by the formation of a second precipitate which is treated with ammonium sulphate solutions having a concentration selected within 56–58 percent of saturation to form the filtrates, followed by precipitation of FSH from the thus-formed filtrates by saturating these with dry ammonium sulphate to a concentration of 70–80 percent of saturated in the solutions, bringing pH value to 4.5 and separating said purified hormone from supernatant liquid.

A number of other hormones are contained in the pituitary gland. Most complete extraction of all said hormones occurs when use is made of an approximately 0.2-molar ammonium sulphate solution.

Bringing the pH of the extraction obtained to 4.5 results in precipitating all the hormones except FSH the pH of which equals 4.5. To provide the most complete extraction of pituitaries, the latter should be subjected to the afore-said treatment at least thrice. FSH proves to be a single hormone of the pituitary that is soluble in an ammonium sulphate solution with a concentration of 40–50 percent of saturated in such a solution; therefore, to make inert proteins (having the pH of 7.4–7.5) precipitate out from the extract, the latter is to be saturated with dry ammonium sulphate to the aforesaid concentrations, followed by bringing the pH of the solution to 7.4–7.5, whereas FSH whose pH equals 4.5 remains in supernatant liquid and is precipitated therefrom by saturation with dry ammonium sulphate to a concentration of 70–80 percent of saturated in the thus-obtained solution (precipitate II).

With a view to eliminating ballast proteins still remaining in said precipitate, it is reasonable to subject the latter to treatment with a 59-percent concentration (of saturated) ammonium sulphate solution.

It is found that a complete dissolution of FSH occurs in the ammonium-sulphate solutions with a concentration of 56–58 percent of saturated, mostly in a 58-percent solution; therefore, said treatment of the precipitate is expedient to occur with the use of ammonium sulphate solutions with concentrations diminishing in a preselected range, while precipitation of said hormone from the obtained filtrates is favourable to carry out likewise by saturating these with dry ammonium sulphate to a concentration of 70–80 percent of saturated in the obtained solutions, with subsequent bringing the pH of the solutions to 4.5, i.e., to the isoelectric point of FSH as it has been stated hereinbefore.

The proposed method is instrumental in producing follicle-stimulating hormone at a yield of 69–94 percent which is much higher than the yield of the final product by the known methods. Besides, the proposed method is not laborious, uses simple technological equipment and involves no expensive reagents.

To promote understanding of the spirit of the present invention same is now illustrated in an exemplary embodiment thereof, that follow.

EXAMPLE

Congealed sheep pituitaries are disintegrated in a homogenizing apparatus and extracted with a 0.2 molar ammonium sulphate solution, followed by bringing the pH of the solution to 5.5 and separation of into supernatant liquid and precipitate. Extraction is carried out three times, the final precipitate is discarded and the supernatant liquids are intermixed and saturated with dry ammonium sulphate to a concentration of 40–50 percent of saturated in the solution, the pH is brought to 7.4–7.5. The resultant precipitate is centrifugation-eliminated. The supernatant liquid is again saturated with dry ammonium sulphate to obtain its concentration in the solution at 70–80 percent of saturated. The thus-obtained precipitate is placed upon a dense filter located in a Buchner funnel, and washed with a 59-percent ammonium sulphate solution till a complete disappearance of protein in the filtrate, whereupon the filtrate is discarded and the precipitate remaining on the filter is washed with ammonium sulphate solutions with a concentration of 58–56 percent of saturated. Then the filtrates are tested for the presence of the hormone therein by means of trichloroacetic acid. The thus-obtained filtrates contain substantially the entire amount of FSH which is then precipitated therefrom by satruating the filtrates again with dry ammonium sulphate to a concentration of 70-80 percent of saturated in the solutions, followed by bringing the pH thereof to 4.5. The precipitate is separated either by centrifuging or by filtration, dissolved in a minimum volume of physiological saline and congealed for storage.

The yield of the final product equals 69–94 percent.

What we claim is:

1. A method of producing follicle-stimulating hormone from sheep pituitary glands comprising:
   A. disintegrating said pituitary;
   B. extracting said hormone from said pituitary by mixing the disintegrated pituitary with about 0.2 molar ammonium sulfate, adjusting the pH to 5.5 to thereby form a precipitate and a supernatant, and separating said precipitate from said supernatant;
   C. purifying said hormone by:
      1. adding dry ammonium sulfate to said supernatant to a concentration of 40–50 percent,
      2. adjusting the pH to 7.4–7.5 to form a precipitate and a supernatant,
      3. adding dry ammonium sulfate to said supernatant from step (C)(2) to a concentration of 70–80 percent to form a precipitate and a supernatant,
      4. washing said precipitate from step (C)(3) with a solution of ammonium sulfate having a concentration in the range of 56–58 percent to form a filtrate,
      5. adding dry ammonium sulfate to said filtrate to a concentration of 70–80 percent, and
      6. adjusting the pH to 4.5 to thereby precipitate said hormone from said filtrate; and
   D. separating said hormone from said filtrate.

2. A method as claimed in claim 1, wherein step (B) is repeated twice and the resultant supernatants are combined prior to step (C).

3. A method as claimed in claim 1, wherein said precipitate from step (C)(3) is washed with a solution of ammonium sulfate having a concentration of 59 percent prior to step (C)(4).

4. A method as claimed in claim 2, wherein said precipitate from step (C)(3) is washed with a solution of ammonium sulfate having a concentration of 59 percent prior to step (C)(4).

5. A method as claimed in claim 1, wherein said precipitate from step (C)(3) is washed a plurality of times with solutions of ammonium sulfate having a concentration in the range of 56–58 percent, with the concentration of each succeeding washing solution being less than the preceding one.

6. A method as claimed in claim 2, wherein said precipitate from step (C)(3) is washed a plurality of times with solutions of ammonium sulfate having a concentration in the range of 56–58 percent, with the concentration of each succeeding washing solution being less than the preceding one.

7. A method as claimed in claim 3, wherein said precipitate from step (C)(3) is washed a plurality of times with solutions of ammonium sulfate having a concentration in the range of 56–58 percent, with the concentration of each succeeding washing solution being less than the preceding one.

8. A method as claimed in claim 4, wherein said precipitate from step (C)(3) is washed a plurality of times with solutions of ammonium sulfate having a concentration in the range of 56–58 percent, with the concentration of each succeeding washing solution being less than the preceding one.

* * * * *